(12) United States Patent
Mahnensmith

(10) Patent No.: US 8,241,262 B2
(45) Date of Patent: Aug. 14, 2012

(54) FLUID COLLECTION AND ASPIRATION UNIT FOR MANAGEMENT OF URINARY INCONTINENCE

(76) Inventor: Michael Mahnensmith, Maui, HI (US)

( * ) Notice: Subject to any disclaimer, the term of this patent is extended or adjusted under 35 U.S.C. 154(b) by 154 days.

(21) Appl. No.: 12/565,450

(22) Filed: Sep. 23, 2009

(65) Prior Publication Data

US 2010/0016818 A1    Jan. 21, 2010

Related U.S. Application Data

(63) Continuation of application No. 10/891,637, filed on Jul. 15, 2004, now abandoned.

(51) Int. Cl.
*A61F 5/458* (2006.01)
*A61M 1/00* (2006.01)
*A47C 27/18* (2006.01)

(52) U.S. Cl. .......... 604/352; 604/327; 5/652.2; 5/655.3

(58) Field of Classification Search .................. 604/327, 604/329, 352; 5/652.1, 652.2, 655.3
See application file for complete search history.

(56) References Cited

U.S. PATENT DOCUMENTS

| | | | | |
|---|---|---|---|---|
| 74,340 A * | 2/1868 | Gilbert | | 5/707 |
| 2,028,060 A * | 1/1936 | Gilbert | | 47/32.5 |
| 2,944,551 A * | 7/1960 | Breer | | 604/73 |
| 3,468,311 A * | 9/1969 | Gallagher | | 604/370 |
| 3,605,145 A * | 9/1971 | Graebe | | 5/706 |
| 3,653,083 A * | 4/1972 | Lapidus | | 5/713 |
| 3,681,797 A * | 8/1972 | Messner | | 297/180.13 |
| 3,757,356 A * | 9/1973 | Freeman | | 4/456 |
| 3,870,450 A * | 3/1975 | Graebe | | 425/269 |
| 3,929,135 A * | 12/1975 | Thompson | | 604/385.08 |
| 4,485,505 A * | 12/1984 | Paul | | 5/714 |
| 4,541,136 A * | 9/1985 | Graebe | | 5/655.3 |
| 4,605,582 A * | 8/1986 | Sias et al. | | 428/120 |
| 4,614,000 A * | 9/1986 | Mayer | | 5/484 |
| 4,620,333 A * | 11/1986 | Ritter | | 5/695 |
| 4,669,460 A * | 6/1987 | Silber | | 128/889 |
| 4,686,724 A * | 8/1987 | Bedford | | 5/652.1 |
| 4,713,065 A * | 12/1987 | Koot | | 604/329 |
| 4,747,166 A * | 5/1988 | Kuntz | | 4/144.1 |
| 4,796,948 A * | 1/1989 | Paul et al. | | 297/284.1 |
| 4,870,710 A * | 10/1989 | Hartmann | | 5/606 |
| 5,005,241 A * | 4/1991 | Difloe | | 5/652.1 |
| 5,111,544 A * | 5/1992 | Graebe | | 5/654 |
| 5,152,023 A * | 10/1992 | Graebe | | 5/655.3 |
| 5,176,667 A * | 1/1993 | DeBring | | 604/356 |
| 5,352,217 A * | 10/1994 | Curro | | 604/378 |
| 5,379,471 A * | 1/1995 | Holdredge | | 5/655.3 |

(Continued)

*Primary Examiner* — Melanie J. Hand
*Assistant Examiner* — Paula Craig
(74) *Attorney, Agent, or Firm* — Hovey Williams LLP

(57) ABSTRACT

A flexible unit for collecting and transporting liquid to a collection point or to an area of use, and especially for facilitating management of urinary incontinence is provided which includes a flexible pad adapted to be positioned under an incontinent patient or worn under an undergarment. The pad is provided with an outer liquid permeable polymeric film layer, an outer liquid impermeable polymeric film layer and an intermediate cellular layer made up of a series of individual, spaced, thin wall, liquid impermeable polymeric cells. An aspiration assembly is connected to the pad for removing urine from the interior of the pad, which collects in the spaces between the individual cells. A disposable porous sheet, preferably comprising Dry-Weave® material, is releasably positioned over the outer permeable film layer of the pad. The pad may be sanitized and reused multiple times with only replacement of the Dry-Weave® sheet being required.

5 Claims, 2 Drawing Sheets

U.S. PATENT DOCUMENTS

| | | | |
|---|---|---|---|
| 5,387,209 A * | 2/1995 | Yamamoto et al. | 604/384 |
| 5,388,296 A * | 2/1995 | Mansour | 5/636 |
| 5,558,654 A * | 9/1996 | Hardy | 604/322 |
| 5,561,875 A * | 10/1996 | Graebe | 5/423 |
| 5,590,428 A * | 1/1997 | Roter | 5/726 |
| 5,675,854 A * | 10/1997 | Zibelin | 5/695 |
| 5,678,564 A * | 10/1997 | Lawrence et al. | 600/574 |
| 5,792,127 A * | 8/1998 | Marran | 604/353 |
| 5,827,246 A * | 10/1998 | Bowen | 604/313 |
| 5,876,393 A * | 3/1999 | Ahr et al. | 604/387 |
| 5,887,304 A * | 3/1999 | von der Heyde | 5/726 |
| 6,180,847 B1 * | 1/2001 | Ahr et al. | 604/367 |
| 6,202,689 B1 * | 3/2001 | Williams | 137/602 |
| 6,450,995 B1 * | 9/2002 | Prabhakar | 604/317 |
| 6,487,739 B1 * | 12/2002 | Harker | 5/726 |
| 6,569,133 B2 * | 5/2003 | Cheng et al. | 604/329 |
| 6,673,982 B1 * | 1/2004 | Chen et al. | 604/378 |
| 6,740,066 B2 * | 5/2004 | Wolff et al. | 604/319 |
| 6,855,135 B2 * | 2/2005 | Lockwood et al. | 604/313 |
| 6,892,734 B1 * | 5/2005 | Schleicher et al. | 128/889 |
| 6,918,899 B2 * | 7/2005 | Harvie | 604/347 |
| 7,939,706 B2 * | 5/2011 | Okabe et al. | 604/361 |
| 2002/0082573 A1 * | 6/2002 | McGrath Hill | 604/366 |
| 2004/0143229 A1 * | 7/2004 | Easter | 604/322 |
| 2004/0236292 A1 * | 11/2004 | Tazoe et al. | 604/317 |
| 2006/0015080 A1 * | 1/2006 | Mahnensmith | 604/327 |

* cited by examiner

FLUID COLLECTION AND ASPIRATION UNIT FOR MANAGEMENT OF URINARY INCONTINENCE

CROSS-REFERENCE TO RELATED APPLICATION

This is a continuation of identically titled application Ser. No. 10/891,637 filed Jul. 15, 2004.

FIELD OF THE INVENTION

This invention relates to thin layer aspiration or perfusion units for collecting vapors or liquids and transferring such fluids to a receiving area. In its preferred form, the invention comprises an aspiration unit for collecting and facilitating management of urinary excretions by individuals that are incontinent.

BACKGROUND OF THE INVENTION

Management of excretions from incontinent patients is an ongoing and largely unsolved problem, not only in hospital and nursing home environments, but also for patients that are not hospitalized or in a care facility. Lack of control over the urinary function by incontinent patients who are not bedridden has for the most part has required the patients to wear large adult diaper pads which soon become fully sorbed and present an odor problem.

In the case of a incontinent patient lying in bed, it has largely been the practice to place an leakproof backed absorbent pad under the patient. The pad soon becomes soaked and timely changing of the soiled pad is often delayed, especially in those instances where the patient is confined to a nursing home where personnel are required to care for a large patient population that is usually the case in a hospital setting. The patient is unable to avoid contact with the wet pad, which is not only uncomfortable, but also is odorous and unsanitary and can cause undesirable skin conditions to occur such as rashes and sores.

Similarly, patients whose condition permits them to sit up in a chair or wheelchair for extended periods of time likewise must be provided with a pad to sit on to collect accidental urine excretions. Here again, changing of a pad as soon as it becomes soaked often cannot be accomplished by the patient and often results in the patient sitting on the wet pad for an extended period until a change out of the pad is ultimately accomplished after an undesirable time interval.

One asserted solution to the incontinent patient problem is shown and described in U.S. Pat. No. 4,747,166. In this patent, a pad is provided having an absorptive core encased within a polyethylene cover in which the normally uppermost layer of the cover is liquid permeable. A perforated tube centrally embedded in the absorptive core is connected via a tube to a urine collection vessel that is in turn coupled to a vacuum pump for withdrawing liquid from the pad absorbed into the central core. The core of the pad is described as having a number of perforated layers of absorbent cellulose tissue in the upper portion of the pad adjacent the upper, permeable layer of the cover, and a plurality of layers of defiberized wood pulp fluff below the cellulose layers. Another cellulose layer is provided below the layers of wood fiber fluff. Alternatively, the core of the pad may be expanded cellulose microcellular material.

Disadvantages of the system of the '166 patent include the cost of the pad, the need to periodically replace the pad, inability to effectively remove all of the liquid absorbed by the core of the pad because a certain proportion of the urine will be retained on the absorbent cellular material, the need for the perforated tube embedded in the core to be relatively rigid in order to preclude collapse of the perforations in the tube thereby imparting a degree of rigidity to the pad, and the impracticality of periodically cleaning the absorbent core of the pad with a cleaning and sterilizing agent.

In addition to the problem of accumulating and disposing of fluid wastes from a bedridden or disabled person, there is a long standing need for inexpensive and efficient apparatus for collecting a variety of fluids, or to deliver fluid from a source to a relatively large surface area in a controlled low volume perfusion transfer manner. Such areas of need include, as an example, dispersion of Treated Sewage Effluent (TSE) in a shallow subsurface underground installation serving as an alternative to a conventional leachfield, to effect evaporation or vertical dispersion of the water in a waste effluent solution, as well as to provide underground irrigation water to the root systems of plants. Another embodiment may be used to control oil slicks on ocean water or the like, as well as aspirating oil out of sand. A further use is to introduce cooled or heated air or water between the layers of structural components such as multilayered roofs, walls or floors to effect heating or cooling, or to provide positive or negative buoyancy of floating structures.

SUMMARY OF THE INVENTION

A vapor and/or liquid collection unit may comprise a thin flexible pad having a liquid permeable first outer polymeric layer and a liquid impermeable second outer polymeric layer, which cooperate to form an interior space. The outer perimeter portions of the permeable and impermeable polymeric layers are heat sealed to form a liquid tight pad. An intermediate cellular layer is positioned in the interior space of the pad between the first permeable outer layer and the liquid impermeable outer layer. The cellular layer is defined by a series of spaced, side-by-side discrete liquid impermeable cellular components containing an entrapped fluid, such as air, which substantially maintains the shape of each cellular component. Each of the cellular components extend from the liquid impermeable outer layer to the permeable outer layer of the pad. The cellular components collectively define intercommunicating liquid passages between the cellular components. These passages also extend from the liquid impermeable outer layer to the permeable outer layer of the pad. The cellular components preferably are made up of a series of individual, thin wall, liquid impermeable, polymeric cells which are joined by a common base sheet.

A disposable liquid permeable porous sheet may be replaceably mounted in overlying relationship to the permeable outer layer of the pad. In a preferred embodiment, the porous sheet is of Dry-Weave® material which has a wicking action for facilitating flow of urine that comes into contact with the porous sheet to the outermost surface of the permeable outer layer of the pad. Snap fasteners may be provided on the perimeter of the pad for releasably affixing the porous sheet to the permeable outer layer of the pad.

A flexible conduit or tube connected to the impermeable layer of the pad, preferably in the center thereof, inter-communicates the interior of the pad with a collection vessel that in turn is operably coupled to an pressure differential device, which for example may be an aspiration unit in the nature of a vacuum pump. The outlet of the vacuum pump may also be joined to a filter adapted to absorb odoriferous constituents in the air emitted from the vacuum pump.

In the preferred embodiment of the vapor and/or liquid collection unit, the cellular layer in the interior space between the permeable outer layer and the impermeable outer layer of the flexible pad comprises a bubble defining sheet consisting of a series of impermeable cellular bubbles, which entrap air, and therefore remain inflated during use of the unit and serve to substantially maintain the integrity of the passages therebetween so that liquid collecting in the pad may be readily and rapidly removed from the interior space of the pad by the differential pressure device. If used, at least two configurations of the flexible pad hereof may be provided. In one configuration, the pad may be square shaped and of dimensions to be used as a bed pad or somewhat smaller as a chair pad. Alternatively, the pad may be of rectangular shape and of a size to be worn by a non-bedridden person beneath an undergarment. In addition, the bed or chair type pads may be provided with grommet openings in the perimeter openings thereof for receiving the hook of flexible retainers for securing the pad in place on an underlying structure such as a bed, or the seat of a chair.

DETAILED DESCRIPTION OF THE PREFERRED THIN LAYER FLUID COLLECTION UNIT OF THE INVENTION

Figure 3:
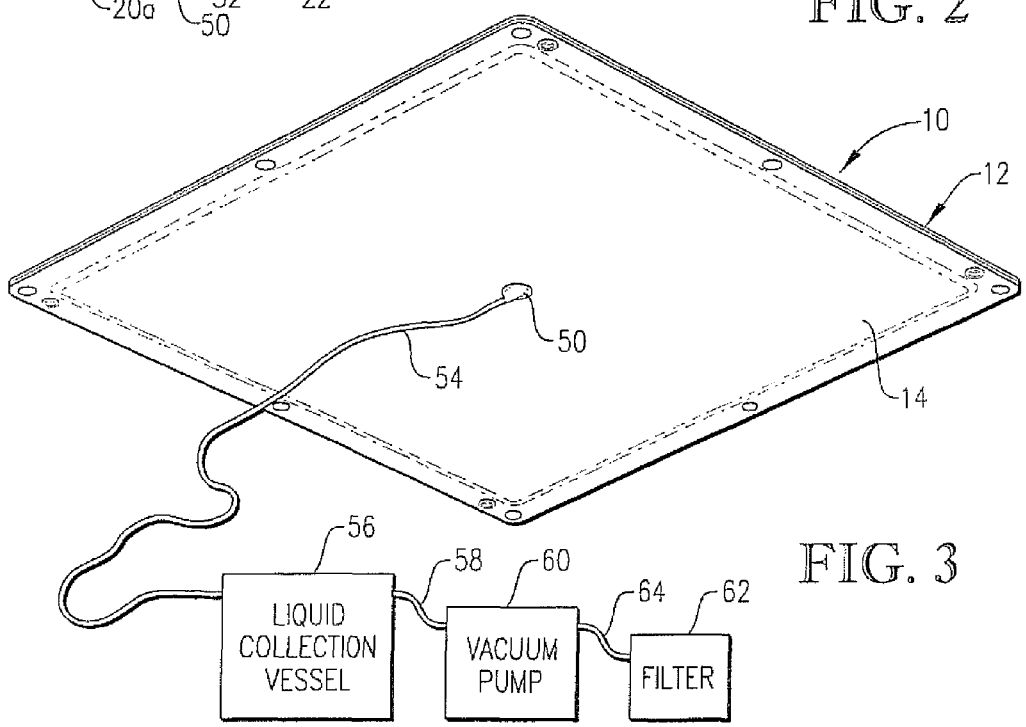
FIG. 3 is a bottom perspective view of the pad and schematically illustrating the aspiration assembly connected to the underside of the pad.

A unit 10 for facilitating management of urinary incontinence is depicted in FIG. 3 and includes as its primary component, a flexible pad 12. The pad 12 includes an outer liquid impermeable layer 14 and a liquid permeable layer 16 in overlying relationship to layer 14. The peripheral margins 14a of layer 14 and 16a of layer 16 of layers 14 and 16 are joined by a liquid tight heat seal 18. The innermost face 14b of layer 14 and the innermost face 16b of layer 16 within the confines of the heat seal 18 joining layers 14 and 16 define an interior space 20.

Figure 2:
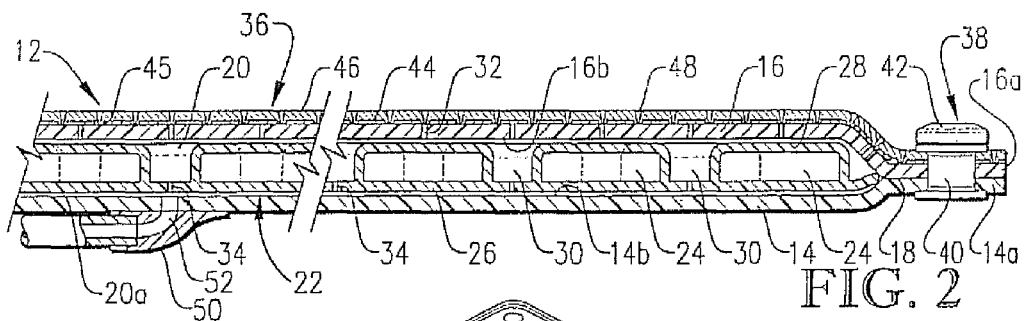
FIG. 2 is a fragmentary enlarged vertical cross-sectional view of the pad as depicted in FIG. 1.

An intermediate cellular layer 22 is confined within interior space 20 between innermost faces 14b and 16b of layers 14 and 16 respectively. Layer 22 is made up of a series of individual, thin wall, liquid impermeable polymeric cells 24, which contain an entrapped fluid, such as air, and that are integral with a polymeric base sheet 26 as is apparent from FIG. 2. Each of the cells 24 has liquid impermeable wall structure 28, which is integral with base sheet 26, and that projects upwardly from sheet 26 into proximity to the innermost face 16b of layer 16. It is to be observed from FIG. 2 that cells 24 in the illustrated embodiment of the invention, are arranged in a series of parallel linear rows with each of the cells 24 of each row being offset longitudinally with respect to adjacent cells in proximal rows. It is to be understood that the individual cells 24 may be of various configurations, as for example, generally cylindrical or of polygonal shape. Each of the cells 24 will be of generally pillow shaped configuration until inserted into the space 20 and confined between layers 14 and 16, whereupon the individual cells normally would assume the shape thereof as shown in FIG. 2. The sheet portion 26 of cellular layer 22 has a plurality of openings 34 therein aligned with passages 30 between cells 24.

The cells 24 of intermediate cellular layer 22 collectively cooperate to define a grid-like series of inter-communicating passages 30 which extend from the upper surface of layer 14 to the underlying surface of impermeable layer 16 of pad 12. Cellular layer 22 may most be conveniently and economically be a form of bubble wrap in which each of the bubbles contains entrapped air so that the bubbles essentially retain their shape when force is applied to the upper face of the permeable upper layer 16 of pad 12.

As best seen in FIG. 2, it will be seen that the base sheet 26 has an outer periphery with the cells 24 located within a cellular of the base sheet inwardly of the base sheet outer periphery; moreover, the maximum lateral dimensions of the cells 24 are greater than the height of the cells 24 above the base sheet 26, with the cell wall structure 28 being free of connection with the upper layer 16. Thus, an unrestricted upper zone is defined between the cell wall structure 28 and upper layer 16, so as to permit fluid to move laterally above the cells 24. In addition, an unrestricted lower zone is defined between the base sheet 26 and the bottom layer 14. Finally, it will be observed that the upper layer openings 32 have a diameter than the thickness of the upper layer 16, and that the base sheet openings 34 have a diameter less than the thickness of the base sheet 26.

The layers 14 and 16 of pad 12 are preferably fabricated of 9 mm thick polymeric material and the overall pad may have length and width dimension of, for example, 28 in. ×28 in. for hospital bed use, and 14 in.×14 in. for use on the seat of a chair or for wheel chair seat use.

Figure 1:
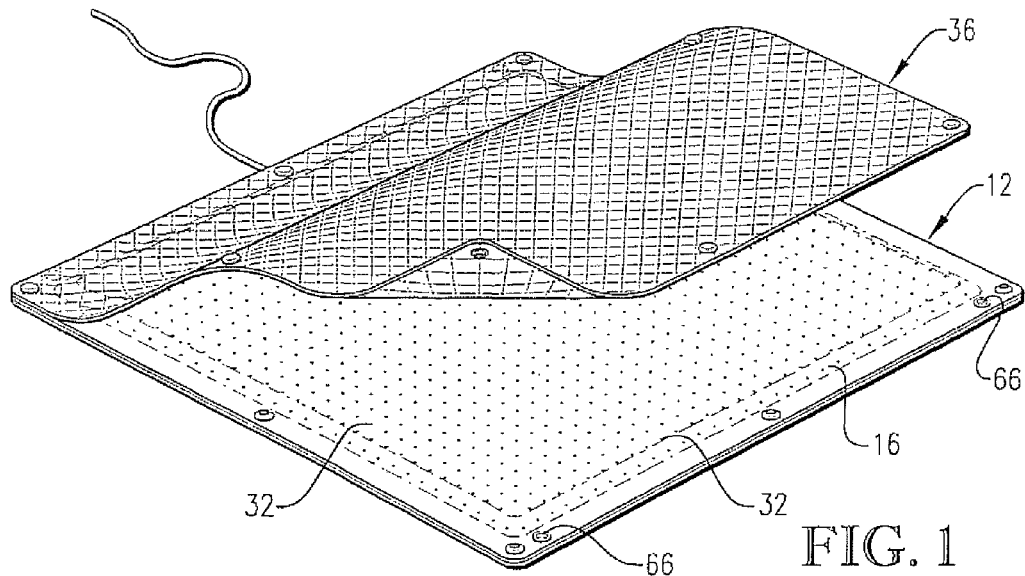
FIG. 1 is a perspective view of a thin layer vapor or liquid collection and aspiration unit for management of urinary incontinence in accordance with one preferred embodiment of the invention, with a corner of the disposable porous member, which overlies the permeable layer of the pad, being lifted to reveal details of the layer of the permeable pad normally overlying the liquid permeable layer of the pad.

The upper layer 16 of pad 12 has a plurality of openings 32 arranged in a gridlike pattern as shown in FIG. 1. The openings 32 in permeable polymeric layer 16 may strategically be located in a 1 in. spacing pattern and preferably are pinhole size.

A porous sheet member 36 overlays the outermost face of permeable layer 16 and is releasably secured to pad 12 by a series of snap fasteners 38. As is most evident from FIGS. 1 and 2, each of the snap fasteners 38 has a female portion 40 extending through and carried by the peripheral margins 14a and 16a of layers 14 and 16, and a removable male portion 42, which affixes the sheet member 36 to pad 12. In the exemplary embodiment of FIG. 1, it is to be observed that snap fasteners 38 are to be provided at each of the corners of rectangular pad 12 and at points midway between the corner snap fasteners 38.

The resilient porous sheet member 36 desirably is of disposable material with Proctor & Gamble's Dry-Weave® material being preferred because of its liquid wicking characteristics. The Dry-Weave® sheet member 36 is shown schematically in FIG. 2 and may for example have a normally innermost apertured polymeric layer 44 and a normally outermost film layer 46 provided with three-dimensional open ended liquid conveying capillary passages 48 communicating with the passages of the polymeric film layer 44. It is to be appreciated in this respect that the passages 48 are shown schematically with only a few of the passages only present being depicted for clarity, in that Dry-Weave® material has a large number of such passages in closely spaced relationship. The passages 48, for example, are each configured to present generally conical surfaces oriented such that the smallest open end thereof is directed toward the innermost polymeric film layer 44 to enhance the wicking action of sheet member 36. Thus, it will be seen that the conical surfaces of the passages 48 are proximal to the upper layer 16, i.e., the smaller open ends of the passageways are closer to the upper layer 16 than the larger open ends thereof. A fitting 50 heat-sealed to the outer face of a central portion of liquid impermeable layer 14 has L-shaped passage 52 therethrough which communicates with the interior space 20 of pad 12. An elongated flexible conduit 54, which for example, may be latex or polymeric surgical hose, is affixed to fitting 50 and communicates with passage 52. Conduit 54 leads to the input of a liquid collection vessel 56 illustrated schematically in FIG. 3. A tubular line 58 communicates the interior of liquid collection vessel 56 with input port of a differential pressure device such as a vacuum pump 60, also shown schematically in FIG. 3. If desired, the air output port of vacuum pump 60 may be connected to a filter unit 62 via line 64. Filter 62 is preferably of a type capable of removing odoriferous agents contained in the air output from vacuum pump 60. Alternatively, unit 10 may be provided with a positive pressure pump in lieu of vacuum pump 60 for perfusion of sanitizing fluid for sterilization and ultimate extraction and drying for storage.

The pad 12 is also preferably provided with grommets 66 in the corner areas of the pad permitting the hook portions of elastic straps, such as bungee cords, to be inserted in respective grommets 66 and affixed to the underside of a supporting structure, such as the patient's bed or components underlying a chair seat or a wheelchair seat. In this manner, the position of the pad 12 will maintain its flat condition even when a patient rests on the pad and assures that the pad will not shift into a crumpled or folded condition, which would be uncomfortable to the patient.

In use, the pad 12 of unit 10 is placed beneath the patient on the surface of a bed or a chair or wheelchair seat, and preferably affixed in a desirable position with suitable fasteners such as bungee cords using the openings of grommet 66 for that purpose. In the event of unintended urinary discharges by the patient, the liquid is received on the surface of porous sheet member 36. If the vacuum pump is activated, the vacuum created in interior space 20 will cause the inadvertently discharged urine to rapidly be drawn through the capillary passages 48 of porous sheet member 36, the perforations in film layer 46, the openings 32 in permeable layer 16 of pad 12, passages 30, openings 34 in base sheet 26, the passage 52 through fitting 50 and conduit 54 leading to collection vessel 56. It is noteworthy in this respect that because of the inflated nature of cells 24, opposed innermost faces of layers 14 and 16 of pad 12 will retain their desired spatial relationship to prevent collapse of passages 30. In addition, because of the inter-connected nature of passages 30 as defined by the individual cells 24, there is no tendency for the urine to be trapped in areas of pad 12 where the vacuum created by pump 60 is incapable of removing the liquid from interior space 20.

It is also to be appreciated that although unit 10 is illustrated as having its own separate vacuum source, such as vacuum pump 60, in a hospital setting, line 58 may be connected to the vacuum line normally present in the wall of the hospital room.

Bed ridden patients can be repeatedly washed on the mats as the excess liquid will be drawn away by the vacuum.

If desired, the porous sheet member 36 may be replaced as necessary to maintain a sanitary environment free of undesirable odors. This replacement may be accomplished by the simple expedient of unfastening snap fasteners 38 and placing the new porous sheet member 36 in place.

An important feature and advantage of the present invention over previously available incontinent management devices is the fact that the pad 36 may be repeatedly washed and cleaned with a suitable deodorizing and sanitizing agent by connecting a pressurized source of such agent to conduit 54 after removal of the porous sheet member 36. Any excess liquid cleaning agent introduced into interior space 20 of pad 12 will simply flow out through the openings 32 in layer 16. Agent remaining in the interior space 20 of pad 12 following the treatment procedure may be removed by recoupling vacuum pump 60 or a source of vacuum to line 58 which will withdraw the sanitizing agent from pad 12.

Alternate Embodiment of the Invention

Figure 4:
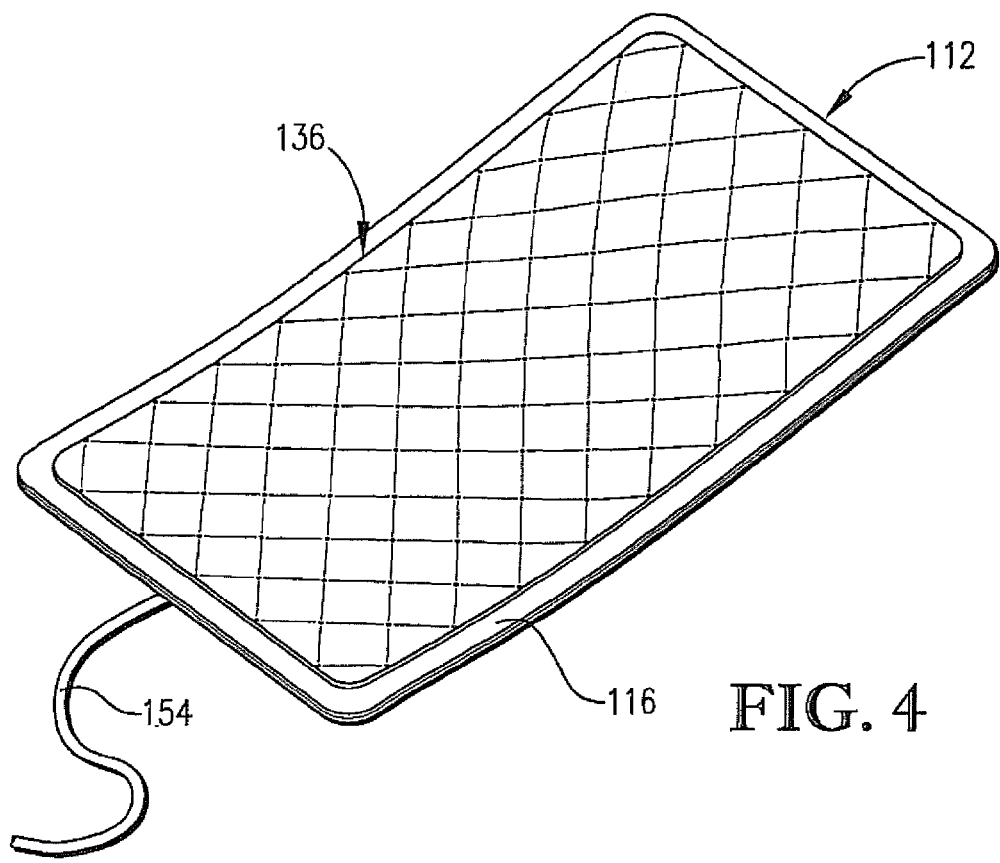
FIG. 4 is a perspective view of a smaller pad than the pad of FIG. 1 and that is adapted to be worn by a incontinent individual.
Figure 5:
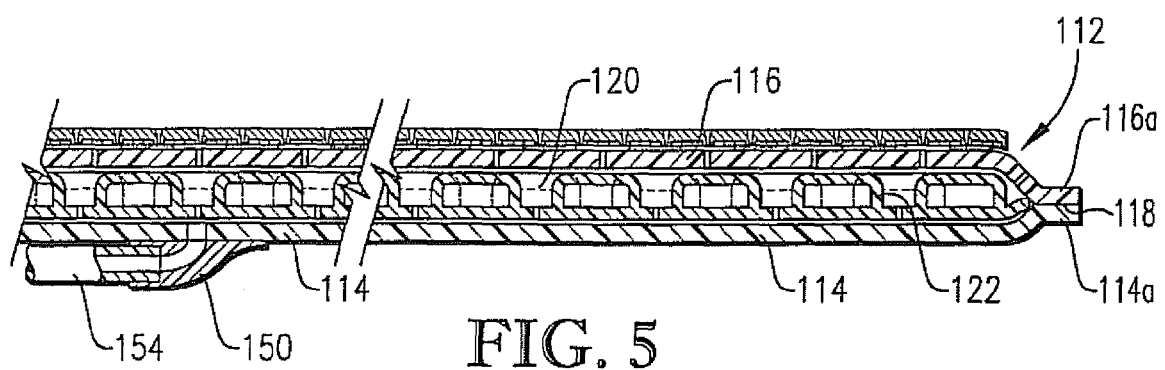
FIG. 5 is a fragmentary enlarged vertical cross-sectional view of the pad as shown in FIG. 4.

The pad 112 illustrated in FIGS. 4 and 5 of the drawings is of construction similar to pad 12 except for its overall size and the manner of attachment of the porous sheet member 136 to the permeable layer 116 of pad 112. In order to permit wearing of pad 112 by an ambulatory patient under his or her undergarment, pad 112 is preferably of a size having overall dimensions of about 10 in.×5 in. The porous sheet member 136, which is also preferably Dry-Weave® material may be removably affixed to the outermost face of permeable layer 116 by use of double-stick tape located around the perimeter of the porous sheet member 136, and at least at the corners of the sheet member 136. Although not shown in FIG. 4, it is to be understood that pad 112 is adapted to be connected to a collection vessel and vacuum pump similar to vessel 56 and pump 60, except for relative sizes, through the medium of a conduit 154, which is again connected to the central portion of liquid impermeable layer 114 of pad 112 through the medium of a passage defining fitting 150. The perimeter margin 116a of layer 116 and perimeter margin of 114a of layer 114 are liquid tight heat sealed as previously with respect to seal 18. The internal space 120 of pad 112 contains a cellular layer 122 preferably formed of bubble wrap material identical in construction to cellular layer 22 described in detail herein above.

The operation and use of pad 112 is the same as described with respect to pad 12 with the understanding that the liquid collection vessel should be of such nature that it can be attached by suitable means to the body of the patient and a battery operated, commercially available, relatively small vacuum pump provided as a source of vacuum. The porous sheet member 136 may be removed and replaced as necessary by simply pulling on the pad to displace the double-stick tape connection of the Dry-Weave® sheet member 136 from layer 116 of pad 112. Sanitizing and deodorizing of pad 112 may be accomplished in the same manner as described with respect to pad 12.

In the case of pad 112, it is desirable that at least the layer 114 of the pad be fabricated of a polymeric material which is non-irritating to the skin of the user. In addition, in the instance of a disposable pad 112, not intended for successive reuses, a line of adhesive may be provided on the peripheral portion of layer 114, which is normally protected by a peelable paper protective strip. The patient can remove the protective strip before positioning of the pad 112 thereby allowing the adhesive line to cause the pad 112 to fully conform to the surface of the patient's body and prevent leakage of liquid around the perimeter edges of the pad 112.

Further Alternative Embodiments of the Invention

The thin layer aspiration or perfusion units for vapor and/or liquid collection have utility for collection and transfer vapors and liquids other than in the management of waste products from an incontinent patient.

Exemplary in this respect is use of the units to distribute septic tank treated effluent waste products from a home, a business or a sewage treatment facility, through an array of shallowly buried (8 to 12 inches deep), mats or pads (long rolls 8 to 20 feet wide) serving as an alternative for a leach-field (to effect vertical evaporation of the water portion of the effluent and to provide nutrient at the base of roots of associated plants to facilitate a Bio-Enhanced Treatment System (BETS). These industrial units are preferably fabricated using heavy (industrial-grade) plastic sheets. The units should include as component parts a perforate top layer, a perforated bubble layer and an imperforate bottom layer, an opening into the bottom layer and a tube connected to that opening. The nature of the outer liquid impermeable layer and the opposed liquid permeable layer of the unit, on opposite sides of the intermediate cellular layer, as previously described, remains the same, except in this instance, the porous Dry-Weave or the like layer is omitted and the tube or tubes connected to the lowermost impermeable layer of the assembled components is adapted to be joined to a septic tank outflow pipe leading from a residence or other source of waste effluent products. Because of the construction of the individual layers, including the bubble layer, each may be manufactured as a substantially continuous component with the longitudinal opposed edges, and respective end edges being joined to provide leak proof edge seals (e.g., long rolls of the order of 8 to 20 feet wide).

Thus, by digging a wide, shallow, elongated trench in the ground 10 to 12 inches deep, of a dimension that accommodates the width of the dispersion unit selected, leveling the exposed surface and unrolling the elongated dispersion unit in the trench with an additional layer of gravel (2 to 3 inches) and soil thereover, treated effluent waste from the septic tank of a residence, etc., delivered to the dispersion unit through the lower imperforate layer will flow along the length and width of the dispersion unit and then leak (perfuse) out through the various openings in the top liquid permeable layer. It is contemplated that a pump be provided in the treated effluent line leading to the dispersion unit to positively direct treated effluent liquid to the inlet of the dispersion unit in a controlled fashion. A buried holding vessel having a liquid level controller may be provided in the treated effluent line between the septic tank and the dispersion unit to assure uniform delivery of treated effluent to the dispersion unit. In addition, a number of dispersion units may be provided in the underground leach bed with lines leading from the holding vessel to respective dispersion units.

In this regard, it is to be understood that the openings provided in the upper permeable layer are sized to provide for proper and desired delivery of treated liquid effluent through the top permeable layer that collects in the dispersion unit and is received from the building's septic tank treated effluent drain pipe (to effect vertical evaporation through the soil and delivery of nutrient to plant roots). Furthermore, it is to be understood that the sheets of polymeric film should be somewhat thicker (e.g., industrial grade) and the cells of the permeable cellular layer normally are larger than the cells of the cellular layer used in the unit for managing urinary excretions of individuals. The cells of the intermediate permeable layer which contain trapped air prevent the dispersion unit from collapsing even when a layer of gravel (2 to 3 inches) and then dirt (up to 12 inches) is filled in over the top of the buried dispersion unit.

An underground dispersion unit similar to the one just described for delivery of treated effluent waste liquid products to a shallow leach bed, may be used to direct fresh irrigation water to the roots of plants. The fresh water underground watering unit normally would not be buried along with layers of gravel and typically would be of a smaller size than the size of the septic field dispersion units. In that connection, it is to be recognized that the fresh water dispersion unit may be sized as appropriate for outdoor watering of plants, as well as for indoor use with plotted plants and the like. Again, a pump is preferably provided to direct the irrigation water to the dispersion unit for delivery through the perforate unit to the surrounding ground.

Alternatively, heated and cooled water or air may be introduced and recollected between layers of gunnite sprayed or poured concrete multi-layered walls, buildings, roofs, ceilings and floors by placing an imperforate dispersion unit plumbed with inlet and outlet only as described, between the layers of the walls, roofs, floors, etc., thus permitting heated or cooled water or air to be introduced uniformly across the surface area and withdrawn. In addition, a perforated dispersion unit as described herein with perforate layer out board may be laminated near the outer surface in a concrete structure such that liquid that is introduced into and then passes through the dispersion unit is expelled from a perforated layer thereof so that it may then weep outwardly into and through the concrete to effect evaporation of the water and consequent cooling of the concrete. In this manner, heating and air conditioning requirements for confined building spaces may be decreased as a result of the heated/cooled air or water being supplied into such spaces via a unit of this invention.

The same type of multi-layered unit used for the dispersion of treated effluent waste liquid in a leach bed, watering of plants and introducing treated water or air into building structural components is also useful in collecting oil from an oil slick released onto the surface of a lake, ocean or another body of water. Conventional inflated tubular rolls are placed around the perimeter of the oil slick and then one or more of the units described herein as having a permeable layer, an intermediate cellular layer and an opposed impermeable layer, are oriented such that the perforated layer faces downward so that the oil floating on the surface of the water is pulled into the interior of the unit through the permeable layer openings. A tube joined to and communicating with the upper imperforate layer of the unit is connected to an aspiration device which causes the oil to be drawn into the dispersion/aspiration unit where it collects in the perforated bubble layer of the unit between the lower permeable layer and the upper impermeable layer. This collected oil is then withdrawn through a tube connected to the aspiration device, and then directed to a suitable collection point or device.

The multi-layered units of this invention are useful in a variety of veterinary and agriculture applications, e.g., use under animals during transport to collect urinary out put in transit. Incorporation or placement of a multi-layered unit as described herein in an indoor cat litter box will thereby eliminate tons of used cat litter now going into landfills annually. Additionally, these multi-layered mats can be placed under leaky hazardous waste containers for spill containment during storage or transport.

It is therefore apparent that the present device is operable to collect a vapor or a liquid product or to deliver a product to a suitable site either by suction created by an aspiration device or under perfusion pressure using a pressure pump. In all instances, the perforated bubble layer prevents the unit from collapsing, regardless of whether a negative pressure or a positive pressure is applied to the unit. An elongated roll unit as described herein and adapted for vertical evaporative dispersion of treated sewage effluent may be manufactured of any desired length and width, and can even be supplied in roll form with the installer cutting segments from the roll of selected lengths and then sealing the transverse edges in the field using a conventional thermal sealing device.

The invention claimed is:

1. An aspirator assembly, comprising:

a pad, including— a liquid impermeable bottom layer having a peripheral margin;

a liquid permeable upper layer having a peripheral edge and an upper face, said upper layer presenting a plurality of openings therethrough operable to permit flow of liquid through the upper layer, the peripheral margin of said bottom layer and the peripheral edge of said upper layer being joined to cooperatively define a plenum chamber between the bottom and upper layers, said upper face of said upper layer being remote from said bottom layer;

a cellular sheet having a base sheet presenting a periphery, and a plurality of substantially uniformly shaped, discrete, air-containing, laterally spaced apart cells defined by respective cell walls extending upwardly from said base sheet throughout a cellular area of the base sheet spaced inwardly from said periphery thereof, said cells having a maximum lateral dimension, with the maximum lateral dimensions of the cells being greater than the heights of the cells above said base sheet, the spaces between said cells defining liquid flow passageways, there being a series of openings through the base sheet communicating with said liquid flow passageways, said cellular sheet located within said plenum with said cell walls proximal to said upper layer and said base sheet proximal to said bottom layer, there being unrestricted upper and lower zones respectively above said cell walls and below said base sheet, said cell walls and said base sheet being free of connection with said upper layer and said bottom layer, respectively, throughout said cellular area, such that fluid passing through said openings may move laterally above said cells in said unrestricted upper zone and between said cells, and fluid passing through said openings may move laterally below said base sheet;

a porous sheet member overlying the upper face of said upper layer, said sheet member including a plurality of capillary passages therethrough, each capillary passage having a conical surface with a smaller open end and a larger open end, each capillary passage oriented such that the smaller open end thereof is proximal to said upper layer, such that the smaller open ends of the capillary passages are closer to the upper layer than the larger open ends thereof; and a negative pressure device operably coupled with said pad and communicating with said lower zone, said device operable to remove fluids collected in said lower zone.

2. The assembly of claim 1, there being a port formed in said bottom layer, said device operably coupled with said port.

3. The assembly of claim 1, said base sheet having a periphery, said base sheet periphery joined with said upper and bottom layers to prevent liquid flow past said base sheet except for liquid flow through said openings.

4. The assembly of claim 1, said upper layer openings having a diameter less than the thickness of said upper layer, and said base sheet openings having a diameter less than the thickness of said base sheet.

5. The assembly of claim 1, said cellular sheet being bubble wrap.

* * * * *